United States Patent
Ban et al.

(10) Patent No.: US 11,576,713 B2
(45) Date of Patent: Feb. 14, 2023

(54) MEDICAL TREATMENT TOOL

(71) Applicants: Hokosangyo Co., Ltd., Nisshin (JP); National University Corporation Nagoya University, Nagoya (JP); Meijo University, Nagoya (JP)

(72) Inventors: Yasuhiro Ban, Nisshin (JP); Kazuya Motomura, Nagoya (JP); Atsuhiko Senba, Nagoya (JP)

(73) Assignees: Meijo University, Nagoya (JP); National University Corporation Nagoya University, Nagoya (JP); Hokosangyo Co., Ltd., Nisshin (JP)

( * ) Notice: Subject to any disclaimer, the term of this patent is extended or adjusted under 35 U.S.C. 154(b) by 183 days.

(21) Appl. No.: 16/623,546

(22) PCT Filed: Mar. 4, 2019

(86) PCT No.: PCT/JP2019/008364
§ 371 (c)(1),
(2) Date: Dec. 17, 2019

(87) PCT Pub. No.: WO2020/178939
PCT Pub. Date: Sep. 10, 2020

(65) Prior Publication Data
US 2020/0383718 A1   Dec. 10, 2020

(51) Int. Cl.
*A61B 18/14* (2006.01)
*A61B 18/08* (2006.01)
(Continued)

(52) U.S. Cl.
CPC ........ *A61B 18/085* (2013.01); *A61B 18/1206* (2013.01); *A61B 2018/00077* (2013.01); *A61B 2018/126* (2013.01)

(58) Field of Classification Search
CPC .............. A61B 18/085; A61B 18/1206; A61B 2018/00077; A61B 2018/126;
(Continued)

(56) References Cited

U.S. PATENT DOCUMENTS 5,306,287 A * 4/1994 Becker ...................... B25B 9/00
606/205
5,603,712 A * 2/1997 Koranda ............ A61B 18/1442
604/35

(Continued)

FOREIGN PATENT DOCUMENTS

| JP | 2004510536 A | 4/2004 |
|---|---|---|
| JP | 2006288425 A | 10/2006 |

OTHER PUBLICATIONS

Lomont Molding LLC, Thermoplastic Resins, 2018 (Year: 2018).*

(Continued)

*Primary Examiner* — Michael F Peffley
(74) *Attorney, Agent, or Firm* — Meunier Carlin & Curfman LLC

(57) ABSTRACT

One aspect of the present disclosure is a medical treatment tool including a first arm having a first end and a second end and a second arm having a first end and a second end, wherein the first end of the first arm and the first end of the second arm are coupled such that a distance between the second end of the first arm and the second end of the second arm is adjustable. Each of the first arm and the second arm comprises: a conductor extending from the first end to the second end and exposed at the second end; a support containing a composite material made of a resin and a reinforcing material as a main component and extending along the conductor; and a cover covering the conductor and the support.

4 Claims, 3 Drawing Sheets

(51) Int. Cl.
*A61B 18/12* (2006.01)
*A61B 18/00* (2006.01)

(58) Field of Classification Search
CPC ........... A61B 2018/00577; A61B 2018/00589; A61B 2018/1462; A61B 18/14; A61B 18/12; A61B 18/00; A61B 2018/1467; A61B 2018/00136; A61B 2018/00607
USPC ..................................................... 606/51, 52
See application file for complete search history.

(56) References Cited

U.S. PATENT DOCUMENTS

| | | | | |
|---|---|---|---|---|
| 6,235,027 | B1* | 5/2001 | Herzon | A61B 18/08 606/49 |
| 7,435,249 | B2* | 10/2008 | Buysse | A61B 18/1442 606/51 |
| 2004/0138528 | A1 | 7/2004 | Richter et al. | |
| 2006/0167452 | A1* | 7/2006 | Moses | A61B 18/1442 606/171 |
| 2006/0276785 | A1 | 12/2006 | Asahara et al. | |
| 2008/0015567 | A1* | 1/2008 | Kimura | A61B 18/1442 606/49 |
| 2017/0265934 | A1* | 9/2017 | Secord | A61B 18/1442 |
| 2018/0368910 | A1* | 12/2018 | Kirwan, Jr. | A61B 18/1445 |

OTHER PUBLICATIONS

David S. Hotter, Geta Grip!, Mar. 10, 1998, Penton Media, Inc. (Year: 1998).*
English Translation of KR Office Action issued in Korean Application No. 10-2019-7037341 dated Mar. 24, 2021 (8 pages).
Notice of Final Rejection in the counterpart Korean Application No. 10-2019-7037341 dated Oct. 26, 2021, 7 pages (original and English machine translation).
Notice of Final Rejection in the counterpart Korean Application No. 10-2019-7037341 dated Jan. 25, 2022 (original and its machine English translation).
English Translation of Notice of Final Rejection in connection with Korean Application No. 10-2019-7037341, dated Jul. 27, 2022, 8 pages.

* cited by examiner

MEDICAL TREATMENT TOOL

TECHNICAL FIELD

The present disclosure relates to a medical treatment tool.

BACKGROUND ART

Medical treatment tools used for dissection and coagulation of biological tissue by applying high frequency voltage to the biological tissue to be treated are known. One type of the medical treatment tools includes bipolar forceps that apply voltage to two action points in an object to be treated (see, Patent Document 1).

PRIOR ART DOCUMENTS

Patent Documents

Patent Document 1: Japanese Unexamined Patent Application Publication No. 2006-288425

SUMMARY OF THE INVENTION

Problems to be Solved by the Invention

Conventional bipolar forceps are relatively heavy because a frame of an arm (that is, a holding portion) is made of metal, which also serves as a conductor. In addition, to retain rigidity, the arm is formed into a certain size. This may cause a user to feel difficulty in holding the arms depending on the user's hand size. Accordingly, the conventional bipolar forceps may impose a great burden on users.

In one aspect of the present disclosure, it is preferable to provide a medical treatment tool that achieves reduction in weight and size while retaining rigidity.

Means for Solving the Problems

One aspect of the present disclosure is a medical treatment tool including a first arm having a first end and a second end and a second arm having a first end and a second end, wherein the first end of the first arm and the first end of the second arm are coupled such that a distance between the second end of the first arm and the second end of the second arm is adjustable. Each of the first arm and the second arm includes a conductor extending from the first end to the second end and exposed at the second end, a support containing a composite material made of a resin and a reinforcing material as a main component and extending along the conductor, and a cover covering the conductor and the support.

According to the above configuration, rigidity of the first arm and the second arm can be retained by supporting the conductor using the support made of the composite material. Thus, it is not necessary to form a frame made of metal in a certain size as conventionally did. In addition, the composite material used in the support is lighter than the metal. Consequently, it is possible to reduce weight and size of the first arm and the second arm. Also, the cover can enhance a degree of freedom in designing of colors, shapes and the like of the medical treatment tool.

In one aspect of the present disclosure, the cover may contain a resin as a main component. This configuration allows the first arm and the second arm to reduce their weight. Also, productivity of the first arm and the second arm can improve.

In one aspect of the present disclosure, the support of the first arm may be arranged on an opposite side of the second arm with respect to the conductor. The support of the second arm may be arranged an opposite side of the first arm with respect to the conductor. With this configuration, in the first arm and the second arm that perform an opening-closing action, each conductor can be supported from outside by the support, which improves the rigidity of the first arm and the second arm.

EXPLANATION OF REFERENCE NUMERALS

1 . . . medical treatment tool, 2 . . . first arm, 2A . . . first end, 2B . . . second end, 3 . . . second arm, 3A . . . first end, 3B . . . second end, 4 . . . joint, 5 . . . cord, 6 . . . plug, 21 . . . conductor, 21A . . . tip, 22 . . . support, 23 . . . cover.

Mode for Carrying Out the Invention

Hereinafter, embodiments of the present disclosure will be explained with reference to the drawings.

1. First Embodiment

[1-1. Configuration]

Figure 1:
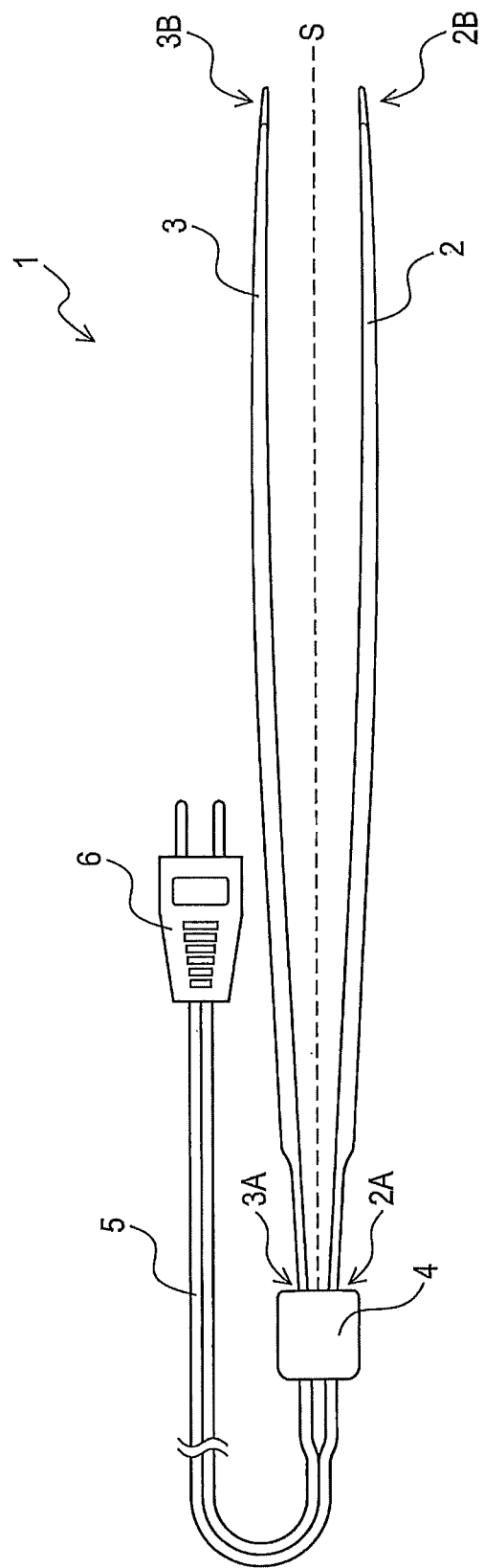
FIG. 1 is a schematic view of a medical treatment tool of an embodiment.

A medical treatment tool 1 shown in FIG. 1 is a treatment tool for dissection, coagulation and the like of biological tissue by applying high frequency voltage.

The medical treatment tool 1 includes a first arm 2, a second arm 3, a joint 4, a cord 5, and a plug 6. The medical treatment tool 1 is an electrosurgical knife with a bipolar electrode (so-called bipolar forceps).

[Arms]

The first arm 2 has a first end 2A and a second end 2B, and is a plate-shaped or rod-shaped member extending from the first end 2A to the second end 2B. Similarly, the second arm 3 has a first end 3A and a second end 3B, and is a plate-shaped or rod-shaped member extending from the first end 3A to the second end 3B.

The first arm 2 and the second arm 3 are coupled by the joint 4 by coupling the first ends 2A, 3A such that a distance between the second ends 2B, 3B is adjustable. In other words, the first arm 2 and the second arm 3 configure a pair of forceps openable and closable with the joint 4 as a fulcrum.

The second end 2B of the first arm 2 and the second end 3B of the second arm 3 are mutually spaced apart while not in use, and brought closer to each other while in use (that is, at the time of execution of treatment). However, the second end 2B of the first arm 2 and the second end 3B of the second arm 3 do not come in contact with each other while in use.

(First Arm)

Figure 2:
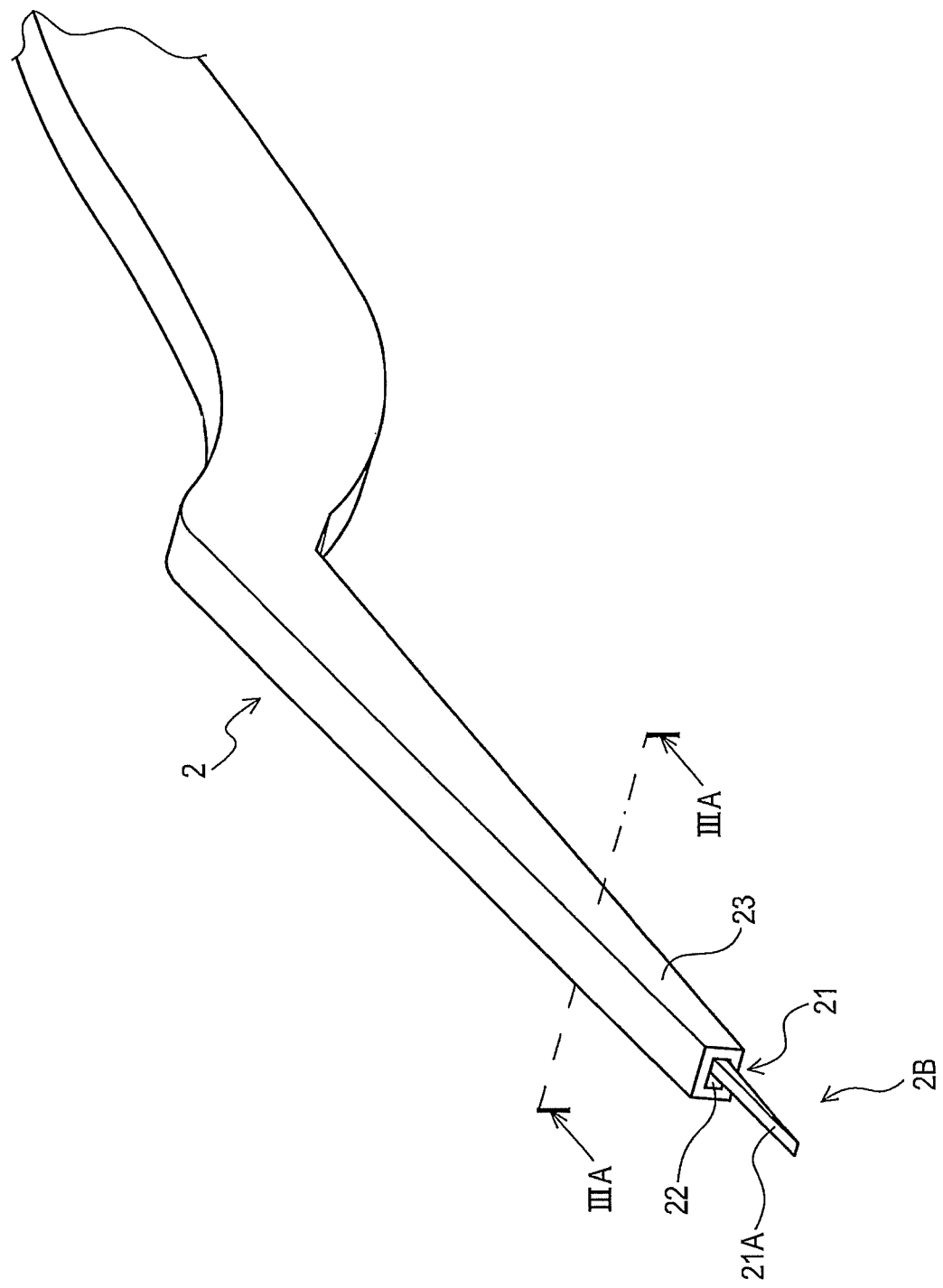
FIG. 2 is a schematic partially enlarged perspective view showing a vicinity of a second end of a first arm of the medical treatment tool in FIG. 1.

As shown in FIG. 2, the first arm 2 includes a conductor 21, a support 22, and a cover 23.

(Conductor)

The conductor 21 is a rod-shaped member extending from the first end 2A to the second end 2B of the first arm 2. The conductor 21 is supplied with current from the cord 5, which will be described below.

The conductor 21 is exposed at the second end 2B of the first arm 2. In other words, the conductor 21 includes a tip 21A that is not covered by the support 22 and the cover 23, which will be described below. The tip 21A comes in contact with the biological tissue, and configures an action point applying high frequency voltage.

Materials that can be used for the conductor 21 may include, for example, metals such as copper, gold, aluminum, platinum, molybdenum, nickel, tungsten, and chrome. The tip 21A of the conductor 21 may be plated with noble metals. Also, materials used for the tip 21A of the conductor 21 and the rest of the portion (that is, a portion covered by the cover 23) may be different.

(Support)

The support 22 is a layer having a composite material (so-called reinforced plastic) made of a resin (that is, matrix) and a reinforcing material as a main component. Here, the "main component" is a component contained in 90% by mass or more. The resin used for the composite material may not be particularly limited, and a thermosetting resin or a thermoplastic resin can be used. The reinforcing material used for the composite material may include, for example, fibers and particles. The fibers used for the composite material may include, for example, a glass fiber and a carbon fiber. The particles may have a spherical, polyhedral, and cylindrical shape.

The support 22 extends along the conductor 21 from the first end 2A to the second end 2B. The support 22 may be divided into multiple portions in a longitudinal direction of the first arm 2. In other words, the first arm 2 may have a region where the support 22 does not exist in a portion other than the second end 2B.

Figure 3A:
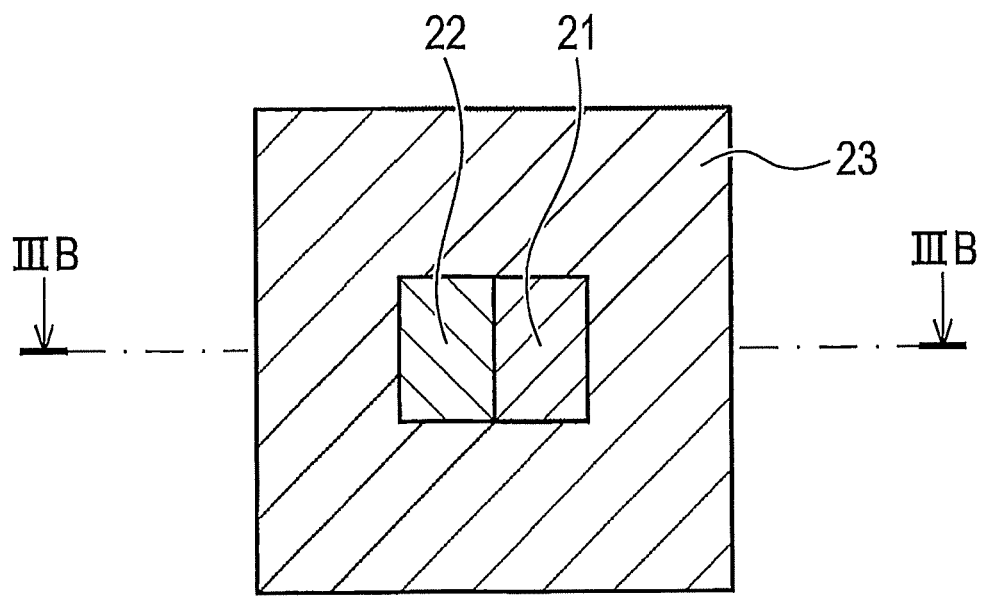
FIG. 3A is a schematic sectional view taken along a line IIIA-IIIA in FIG. 2.
Figure 3B:
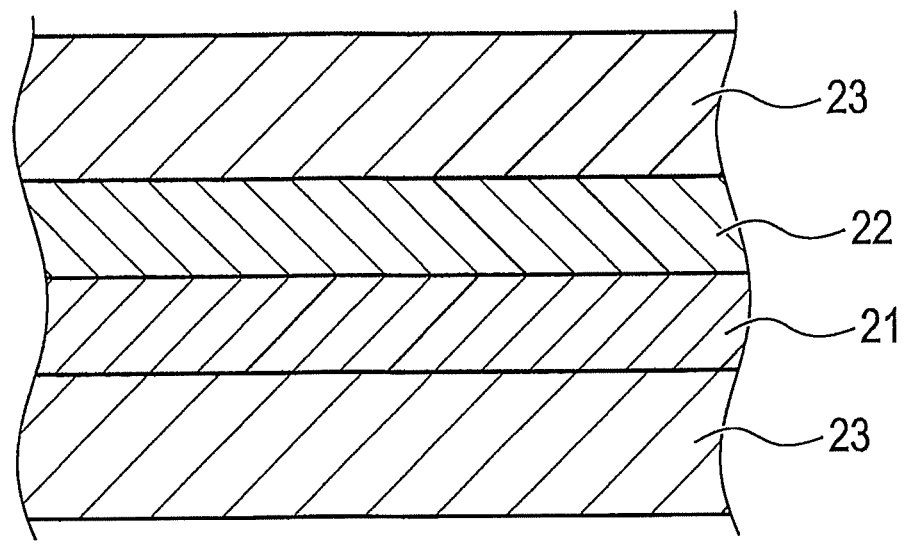
FIG. 3B is a schematic sectional view taken along a line IIIB-IIIB in FIG. 3A.

In the present embodiment, as shown in FIG. 3A and FIG. 3B, the support 22 is disposed so as to be overlaid with a surface of the conductor 21 and abuts the surface of the conductor 21. The support 22 covers a part of the periphery of the conductor 21. Also, the support 22 is arranged on an opposite side of the second arm 3 with respect to the conductor 21 (in other words, on a side of a direction where the forceps open).

The support 22 is not overlaid with the first end 21A of the conductor 21. Also, the support 22 is covered by the cover 23, which will be described below, and is not exposed outside at the second end 2B of the first arm 2. Thus, the support 22 does not come in contact with the biological tissue.

(Cover)

The cover 23 is a member covering the conductor 21 and the support 22. The cover 23 covers the entire support 22, and a portion of the conductor 21 other than the tip 21A. The cover 23 configures a holding part that a user holds.

Materials of the cover 23 are not particularly limited. Preferably, the cover 23 may contain, for example, a resin such as polyamide, polyethylene, polyether ether ketone (PEEK) as a main component. With the cover 23 having an insulating property (in other words, when the cover 23 contains an insulating resin as a main component), the support 22 can be made of a composite material containing a conductive reinforcing material (for example, fiber reinforced plastic containing carbon fibers such as carbon nanotubes).

When the cover 23 contains the insulating resin as a main component, it is possible to further reduce weight of the first arm 2. In addition, since the cover 23 can be easily formed, productivity of the first arm 2 can improve.

In FIG. 2, the conductor 21 protrudes from an end face formed by the support 22 and the cover 23; however, this configuration is one of the examples. For example, the support 22 and the cover 23 may be continuously thinner toward the tip 21A of the conductor 21. Alternatively, only the cover 23 may be continuously reduced in diameter toward the tip 21A.

(Second Arm)

The second arm 3 has the conductor 21, the support 22, and the cover 23 similar to the first arm 2. However, in the second arm 3, the support 22 is arranged on an opposite side of the first arm 2 with respect to the conductor 21.

In other words, the second arm 3 and the first arm 2 are symmetrical in shape with respect to a virtual plane S that is orthogonal to a direction where the first arm 2 and the second arm 3 are opposed to each other and that is equidistant from the tip 21A of the first arm 2 and the tip 21A of the second arm 3 (see FIG. 1).

(Manufacturing Method)

The first arm 2 and the second arm 3 can be manufactured by the following procedure, for example. First, a composite material sheet forming the support 22 is stacked on the conductor 21. Then, two resin sheets forming the cover 23 are stacked such that the conductor 21 and the composite material sheet are sandwiched by the two resin sheets. Each member is press-bonded while heating this stacked body, thereby obtaining the first arm 2 and the second arm 3.

Alternatively, it may be possible to prepare a joined body formed by the conductor 21 and the support 22, and then cover this joined body with the cover 23. A specific method of covering with the cover 23 may include, for example, spraying a resin around the joined body, insertion molding by inserting a resin with respect to the joined body, and covering the joined body by a shrinkable tube.

[Joint]

As shown in FIG. 1, the joint 4 is attached to the first end 2A of the first arm 2 and the first end 3A of the second arm 3.

The joint 4 forms a fulcrum of the forceps configured by the first arm 2 and the second arm 3. Also, the cord 5 is pulled into the joint 4. The conductor 21 of the first arm 2 and the conductor 21 of the second arm 3 are insulated each other in the joint 4.

[Cord]

The cord 5 is a bipolar cord having two electric wires. Each of the electric wires is electrically connected to each of the conductor 21 of the first arm 2 and the conductor 21 of the second arm 3 in the joint 4.

[Plug]

The plug 6 is electrically connected to the cord 5. The plug 6 is connected to a high frequency current generator (not shown).

High frequency current generated by the high frequency current generator flows through the cord 5 to the conductor 21 of the first arm 2. The high frequency current flowed to the conductor 21 of the first arm 2 flows from the tip 21A of the conductor 21, via the biological tissue, to the tip 21A of the conductor 21 of the second arm 3, and returns to the high frequency current generator. It should be noted that the current may flow from the conductor 21 of the second arm 3 to the conductor 21 of the first arm 2.

[1-2. Effect]

According to the embodiment explicitly explained above, the following effects can be obtained.

(1a) The rigidity of the first arm 2 and the second arm 3 can be retained by supporting the conductor 21 by the support 22 formed of the composite material. Thus, it is not necessary to make a frame by metal in a certain size as conventionally did. In addition, the composite material used for the support 22 is lighter than the metal. Consequently, it is possible to reduce weight and size of the first arm 2 and the second arm 3. Also, with the cover 23, the degree of freedom in designing of colors, shapes and the like of the medical treatment tool 1 can be enhanced.

(1b) The support 22 of the first arm 2 is arranged on the opposite side of the second arm 3 with respect to the conductor 21, and the support 22 of the second arm 3 is arranged on the opposite side of the first arm 2 with respect to the conductor 21, thus, in the first arm 2 and the second arm 3 that perform an opening-closing action, each conductor 21 can be supported from outside by the support 22. Thus, it is possible to improve rigidity of the first arm 2 and the second arm 3.

2. Other Embodiment

Although the embodiment of the present disclosure has been explained hereinbefore, it should be noted that the present disclosure may be achieved in various modifications without being limited to the aforementioned embodiment.

(2a) In the medical treatment tool 1 in the aforementioned embodiment, the support 22 of the first arm 2 is not necessarily be arranged on the opposite side of the second arm 3 with respect to the conductor 21. Similarly, the support 22 of the second arm 3 is not necessarily arranged on the opposite side of the first arm 2 with respect to the conductor 21.

The support 22 may cover the entire periphery of the conductor 21 (in other words, so as to wrap up the conductor 21). In addition, the support 22 does not necessarily come in contact with the conductor 21. In other words, other member (for example, a portion of the cover 23) may be arranged between the support 22 and the conductor 21.

(2b) One function of one element in the aforementioned embodiment may be divided as two or more elements. Functions of two or more elements may be integrated into one element. A part of the configuration of the aforementioned embodiment may be omitted. At least a part of the configuration of the aforementioned embodiment may be added to or replaced with other configuration of the aforementioned embodiment. It should be noted that any and all forms that are encompassed in the technical ideas defined only by the languages in the scope of the claims are embodiments of the present disclosure.

The invention claimed is:

1. A medical treatment tool comprising:
   a first arm having a first end and a second end; and
   a second arm having a first end and a second end,
   wherein the first end of the first arm and the first end of the second arm are coupled such that a distance between the second end of the first arm and the second end of the second arm is adjustable,
   wherein each of the first arm and the second arm comprises:
   a conductor extending from the first end to the second end and exposed at the second end;
   a support containing a composite material made of a resin and a reinforcing material as a main component and extending along the conductor; and
   a cover covering the conductor and the support,
   wherein the reinforcing material is fibers or particles,
   wherein the conductor includes a tip that protrudes in an extension direction from the support and the cover and is not covered by the support and the cover,
   wherein the cover comprises a holding part that a user holds,
   wherein the support abuts a surface of the conductor at an area closer to the tip than to the holding part at least along an extension direction of the conductor.

2. The medical treatment tool according to claim 1, wherein the cover contains a resin as a main component.

3. The medical treatment tool according to claim 1, wherein the support of the first arm is arranged on an opposite side of the second arm with respect to the conductor, and the support of the second arm is arranged on an opposite side of the first arm with respect to the conductor.

4. The medical treatment tool according to claim 1, wherein the cover covers the entire support.

* * * * *